United States Patent [19]

Takatsu

[11] Patent Number: 4,832,600
[45] Date of Patent: May 23, 1989

[54] APPLICATOR FOR DENTAL CEMENT LINING

[75] Inventor: Toshio Takatsu, Narashino, Japan

[73] Assignees: Toshio Takatsu, Narashino; G-C Dental Industrial Corp., Tokyo, both of Japan

[21] Appl. No.: 94,833

[22] Filed: Sep. 10, 1987

[30] Foreign Application Priority Data

Oct. 3, 1986 [JP] Japan .................. 61-151586[U]
Dec. 17, 1986 [JP] Japan .................. 61-298694

[51] Int. Cl.⁴ .............................................. A61C 3/08
[52] U.S. Cl. .................................................... 433/164
[58] Field of Search .................. 433/141, 80, 83, 164, 433/102

[56] References Cited

U.S. PATENT DOCUMENTS 797,270 8/1905 Dreher ................................ 433/141

FOREIGN PATENT DOCUMENTS 2447662 10/1975 Fed. Rep. of Germany ...... 433/141
2939211 4/1980 Fed. Rep. of Germany ...... 433/141

Primary Examiner—Gene Macene
Assistant Examiner—Adriene J. Lepiane
Attorney, Agent, or Firm—Oblon, Fisher, Spivak, McClelland & Maier

[57] ABSTRACT

An applicator for dental cement lining includes a shaft having its head divided into an available face in the spherical form and an unavailable opposite face in the flat form. The flat place of the unavailable face may subtend a given angle of 0° to 30° with respect to the axial direction of the shaft. The available and unavailable faces of the head may be joined to each other through cut-outs formed in both sides of the head. The portion of the shaft contiguous to the head may be turned by a given angle with the middle portion thereof, and is fixed in place at that angle.

9 Claims, 4 Drawing Sheets

FIG. 1
FIG. 2
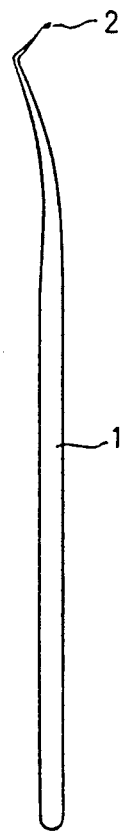
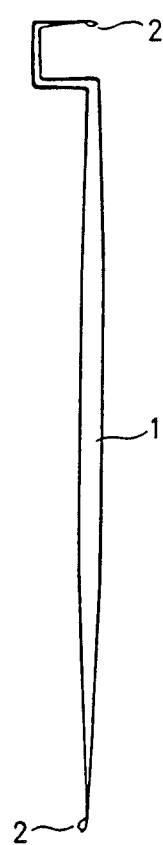

APPLICATOR FOR DENTAL CEMENT LINING

BACKGROUND OF THE INVENTION

1. Field of the Invention

The present invention relates to an applicator for dental cement lining essential for the pulp protection prior to the tooth restoration, which makes it possible to precisely and rapidly line only the required region such as a deep floor in the proximal cavity with a lining material such as dental cement.

2. Statement of the Prior Art

Required for the restoration of defects in the tooth hard tissues are generally such treatments as indirect pulp capping intended to line an area with the pulp unexposed in a deep portion in the cavity floor with a lining material such as dental cement or direct pulp capping intended to protect a small area with the pulp exposed by lining of a material such as dental cement.

In general, applicators for dental cement lining are used for the treatment such as the indirect pulp capping or the direct pulp capping to be applied to the required region such as the deep portion in the cavity floor. Of these applicators, the one enjoying the most frequent use has its functional head in the form of a small sphere.

Such a prior art applicator for cement lining having a spherical head includes a shaft and a spherical portion provided at the extreme end thereof and having its center lying on a line extending axially therefrom. Hence, it appears that said applicator is easy to handle, since it theoretically permits lining of the cement material in every direction. In actual use, however, the spherical head is found to offer the following various problems.

In most cases, the applicator has its head put into a lining material for collection, so that the lining material is uniformly deposited on the entire head. This results in the following problems.

By way of example, explanation will now be made to the lining of a cement with respect to the axial cavity walls of proximal cavities in the anterior and posterior teeth.

(1) As illustrated by Area A in FIG. 11, the cement tends to be deposited on the unrequired region such as the adjacent tooth surfaces other than Area D to be lined, thus presenting a contamination phenomenon. Since the cement deposited on the adjacent tooth surfaces creates an obstacle to filling of a restoring material, it has to be completely removed in advance. This imposes extremely troublesome and extra manipulations upon a dentist.

(2) During the application of the cement, it is likely that a portion of the lining material deposited on the applicator may come into contact with cavity wall surfaces other than the required region, and remain there, as shown by Area B in FIG. 11. Since the portion of the lining material applied on the unrequired regions may be responsible for deteriorations of the adaptation, adhesion and marginal closure of the restoration to the cavity wall, they should be removed. This may lead to a considerable drop in working effeciency.

(3) The field of view may be blocked by a portion of the lining material deposited on the face of the applicator's head opposite to its available face, as depicted by Area C in FIG. 11, thus leading to a failure in precise lining of the required region with the lining material. Especially, such a phenomenon occurs in the treatment of proximal cavities.

(4) In most cases, the portion of the lining material deposited on the face of the applicator's head opposite to its available face is disposed without use. Thus, wasteful consumption of the material is very likely to result.

(5) Due to the fact that the spherical portion of the head of the applicator is as small as 1 mm at the most, it is difficult to control the amount of the lining material to be collected.

SUMMARY OF THE INVENTION

As a result of intensive studies made to solve the problems of the conventional applicators for cement lining, it has been found that they are caused by the spherical form of their head in that the available face side is indiscriminable from the opposite or unavailable face side on which any manipulation is not virtually needed, and that the function-inhibiting factors can be eliminated by flattening the unavailable face side which is of less serviceability and gives an obstacle to the field of view during treatment without causing substantial change in the effective serviceable area.

More specifically, a main object of the present invention is to provide an applicator for dental cement lining, characterized in that the head of its shaft includes a spherical available face and an unavailable flat face which is opposite thereto.

BRIEF DESCRIPTION OF THE DRAWINGS

Preferred embodiments of the present invention will now be described, by way of example, with reference to the accompanying drawings in which:

FIG. 1 is a side view illustrating one embodiment of the applicator for dental cement lining according to the present invention, FIG. 2 is a side view illustrating another embodiment of the applicator for dental cement lining according to the present invention.

PREFERRED EMBODIMENTS OF THE INVENTION

Figure 3:
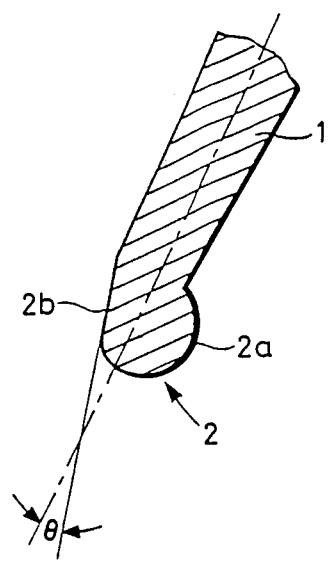
FIG. 3 is an enlarged vertical longitudinal sectional view of the head shown in FIG. 1.
Figure 4:
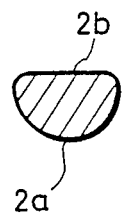
FIG. 4 is an enlarged transverse sectional view of the head shown in FIG. 1.
Figure 5:
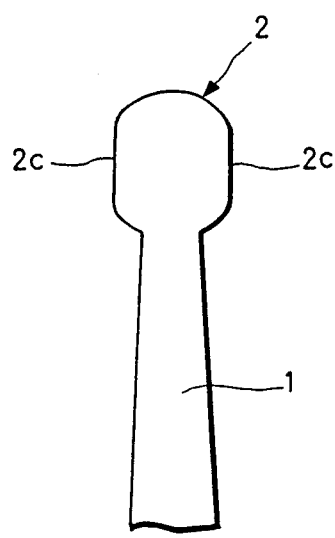
FIG. 5 is a plan view showing the head of a further embodiment of the applicator for dental cement lining according to the present invention.
Figure 6:
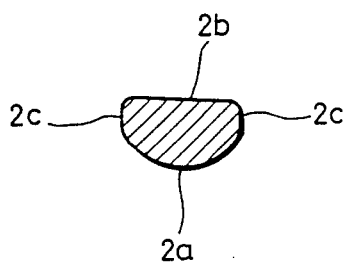
FIG. 6 is a transverse sectional view of the head shown in FIG. 5, FIGS. 7 to 9 are side views illustrating various relationships between the head and shaft in the applicator for dental cement lining according to the present invention.
Figure 7:
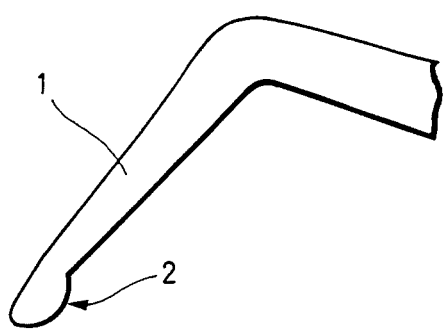
Figure 8:
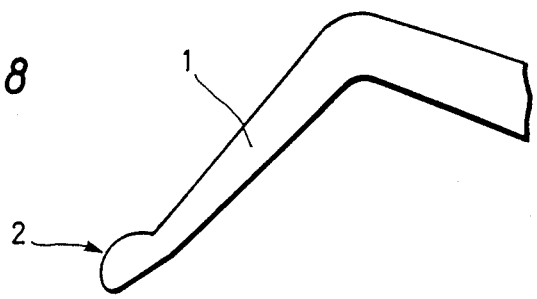
Figure 9:
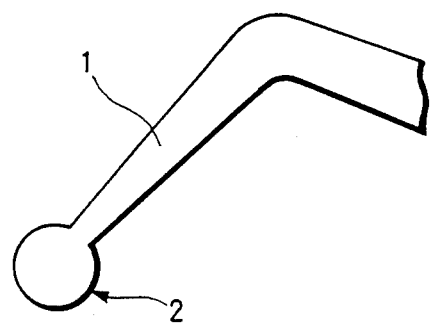

Referring to the drawings, the extreme end of a shaft 1 is usually bent in an arcuate shape or a dogleg shape or a U shape, as illustrated in FIG. 1, but may be of a straight or linear shape. A head or heads 2 may be provided at one or both extreme ends of one or both sides of the shaft 1. Each head 2 is comprised of a spherical portion with available face 2a and an non-spherical portion having an unavailable flat face 2b which is opposite thereto. When the spherical shape of the head 2 has a diameter of as small as 1 mm at the most, it is preferred that both faces 2a and 2b are joined to each other through smooth, but not acute, bends so as to securely and easily remove the set lining cement after use, as ilustrated in FIG. 4. When the spherical shape of the head 2 has a diameter exceeding 1 mm, however, it is preferred that both faces 2a and 2b are connected to each other through cut-outs forming non-spherical faces 2c provided on both sides of the head 2, as illustrated in FIG. 6, since its lateral diameter can be reduced without causing any substantial reduction in the effective area of the available face 2a, thereby readily allowing its insertion into a narrow portion in the proximal cavity. When such heads 2 are provided on both sides of the shaft 1, it is preferred that they are different in size from each other, as illustrated in FIG. 2, since different manipulations can be done with a single applicator for dental cement lining. When the head 2 is provided on the extreme end of the shaft 1 bent into a dogleg shape as depicted in FIG. 1 or a U shape in depicted in FIG. 2, it is usually preferred that the available face 2a of the aforesaid shape is provided on the inside of the bent portion, as shown in FIG. 7. Provision of the available face 2a on the outside of the bent portion as shown in FIG. 8 or in parallel with the axial direction of the bent portion as shown in FIG. 9 may be convenient for various manipulations for cement lining. For instance, the portion of the shaft 1, to which the head is attached, may be turned by the given angle with respect to the middle portion thereof and fixed in place at that angle so as to allow a single applicator for cement lining to meet such convenience. In other words, the shaft is divided into two portions. One shaft portion is formed in one end with a hole of an inverted truncated cone, while the other shaft portion is formed in the associated end with a truncated-conical hole having the same taper. The shape portions are then fitted together end-to-end. It is preferred in this case that when the shaft 1 is bent into a dogleg or U shape, the shaft portions are fitted together at a suitable position that is located before the first bent portion, as viewed from the head 2. It is also preferred that, regardless of whether or not the shaft 1 includes a bend or bends, the unavailable face 2b subtends at a given angle of 0 to 30° with respect to the axial direction of the shaft 1 so as to taper to smoothly merge with the shaft to allow easy removal of excessive lining cement deposition thereon.

Figure 10:
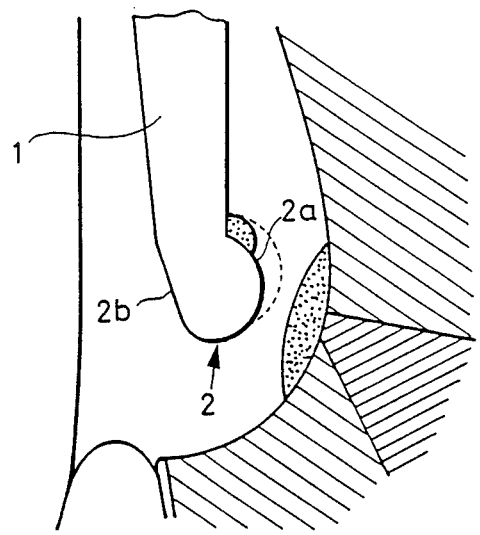
FIG. 10 is a view illustrative of the lining of an important portion in the proximal cavity with a dental cement lining material by means of the applicator according to the present invention.
Figure 11:
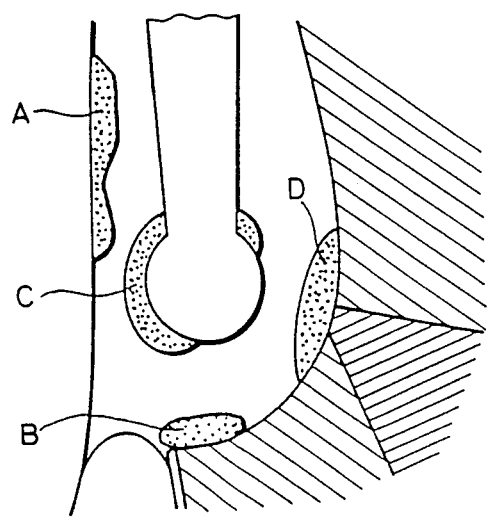
FIG. 11 is a view illustrative of one conventional applicator for dental cement lining, which is shown to be used to line an important portion in the proximal cavity with dental lining cement.

When the cement for pulp capping is collected as the lining material with the use of the present applicator having the structure as mentioned above, the head 2 is put forward into mixed cement slurry thinly spread over a mixing pad, and is then forced back, whereby the required amount of cement is collected on the spherical portion of the available face 2a as depicted by broken line in FIG. 10. In this case, when it appears that excessive cement deposited on the unavailable face 2b gives an obstacle to treatment, such deposits may only be rubbed out on the mixing pad.

When the dental cement is applied over the axial walls of the proximal cavities with the use of the present applicator having the required amount of cement placed on the available face 2a of the head 2 and including the bend or bends as shown in FIG. 1 or 2, the portion of the shaft 1 near the applicator's head 2 is first placed on the adjacent tooth surfaces for stable supporting. While visually examining the required region to be treated from the rear of the unavailable face 2b of the head 2, the head 2 is then inserted through the cavities to guide the available face 2a to the required region, whereby the cement can be precisely applied over the required region. In this case, the field of view is unlikely to be blocked due to the fact that the unavailable face (2b) side is flat. In addition, because the cement is placed on the available face (2a) side alone, the cement is unlikely to be applied over unrequired regions other than the required ones.

When the cement is applied over deep portions of the floor in the class 5 or wedge shaped defect cavities, treatment can be carried out without either blocking the field of view of contaminating unrequired regions other than the required ones with the cement.

Further, when the cement is applied over only portions of the relatively large and flat cavity floor, it is almost unlikely that other portions may be contaminated with the cement. Thus, it is a matter of course that the cement can be deposited over the entire head 2, and be directly applied over the required region, as is actually the case with the prior art applicator, the head of which is spherically shaped as a whole.

In the the applicator according to the present invention as detailed above, the shape of the head available to the dental lining cement is, not in entirely undirectional spherical form as in the conventional applicators, divided into a face primarily available to the cement and a face of less availability opposite thereto; the former face having a spherical contour and the latter face having a flat contour, and has various advantages as enumerated below, which are believed to make a great contribution to dentistry.

(1) Manipulatability is very improved, since the unavailable face is so flat that visual examination of the required region can be carried out from the rear thereof while the field of view is not blocked, when the dental lining cement is applied over the required region of the deep floor to restore a defect in the tooth hard tissues.

(2) The unavailable face is so flat that even when some lining cement deposits are found thereon at the time of collection, they can easily be rubbed off on a mixing pad.

(3) As stated in the foregoing, since the dental lining cement can be placed only on the available face without any deposit on the unavailable face, it is possible to apply the cement only over the region to be applied and lined therewith without fear of contaminating other regions. As a result, it is not required to clean the contaminated regions of the cement, thus leading to considerable improvements in manipulatability.

(4) As already stated in (1), the absence of any portion which is likely to block the field of view during treatment makes it unnecessary to decrease the size of the head to an extreme degree and, hence, makes it somewhat larger than that of the conventional applicator. This results in an increase in the amount of the lining cement available, which makes it possible to improve manipulatability and makes it easy to obtain the cement lining of homogeneous thickness.

(5) As already stated in (1), it is unnecessary to decrease the size of the head to an extreme degree. Thus, when different size of heads are provided on both sides of the shaft, it is possible to perform various manipulations with a single lining applicator.

(6) The present applicators can be made in the same manner as the conventional ones, since the difference therebetween is only in the shape of their heads.

(7) The available and unavailable faces of the head may be joined to each other through the dividing boundary of a smoothly curved face having no acute portion, not only is the applicator's appearance can be improved, but also the set lining cement can be securely and readily removed after use.

(8) When the spherical shape of the available face of the head has a large diameter as expressed by at least 1 mm, cut-outs may be formed in both sides of the head to decrease the lateral diameter of the head with no substantial reduction in the effective area of the available face, thereby enabling the head to be inserted in a narrow important portion in the proximal cavity.

(9) Provision may be made of various forms of the applicators in which the available faces of the heads are located on the inside, outside and sides of the extreme ends of the shafts as illustrated in FIGS. 7, 8 and 9. Thus, irrespective of the position at which the required region to be lined is located on a tooth, a dentist can select the best applicator for the purpose to easily and precisely perform lining without varying his or her operational location or forcibly flexing his or her wrist.

(10) The portion of the shaft contiguous to the head may be turned by a given angle with respect to the middle portion thereof, and fixed in place at that angle, whereby a single lining applicator is allowed to have the effect as referred to in (9).

What is claimed is:

1. An applicator for dental cement lining, comprising an elongate shaft; and a head at one axial end of said shaft, said head comprising a spherical portion and a non-spherical portion, wherein said non-spherical portion comprises a flat face subtending a predetermined positive angle with respect to an axis of a portion of said shaft adjacent said one end and tapers to smoothly merge with said portion of said shaft.

2. The applicator of claim 1 wherein said predetermined angle is approximately 30°.

3. The applicator of claim 2 wherein said portion of said shaft adjacent said one end is bent with respect to a remainder of said shaft, and wherein said predetermined angle has a sense opposite that of the bend, whereby said flat face has an outside position relative to said bend.

4. The applicator of claim 3 including non-spherical faces connecting said spherical portion with said flat face.

5. The applicator of claim 2 including non-spherical faces connecting said spherical portion with said flat face.

6. The applicator of claim 2 wherein said portion of said shaft is straight.

7. The applicator of claim 1 wherein said portion of said shaft adjacent said one end is bent with respect to a remainder of said shaft, and wherein said predetermined angle has a sense opposite that of the bend, whereby said flat face has an outside position relative to said bend.

8. The applicator of claim 1 including non-spherical faces connecting said spherical portion with said flat face.

9. The applicator of claim 1 including a head on another axial end of said shaft.

* * * * *